United States Patent
Allegrini et al.

(10) Patent No.: US 9,334,223 B2
(45) Date of Patent: May 10, 2016

(54) PROCESS FOR THE PURIFICATION OF 2-PHENYL-2-METHYL-PROPANOIC ACID DERIVATIVES

(71) Applicant: DIPHARMA FRANCIS S.r.l., Baranzate (MI) (IT)

(72) Inventors: Pietro Allegrini, Baranzate (IT); Vittorio Lucchini, Baranzate (IT); Davide Rossi, Baranzate (IT); Mauro Mittino, Baranzate (IT); Gabriele Razzetti, Baranzate (IT)

(73) Assignee: Dipharma Francis S.r.l., Baranzate (MI) (IT)

(*) Notice: Subject to any disclaimer, the term of this patent is extended or adjusted under 35 U.S.C. 154(b) by 0 days.

(21) Appl. No.: 14/505,578

(22) Filed: Oct. 3, 2014

(65) Prior Publication Data

US 2015/0099899 A1    Apr. 9, 2015

(30) Foreign Application Priority Data

Oct. 7, 2013  (IT) ............................... MI2013A1652

(51) Int. Cl.

| | | |
|---|---|---|
| *C07C 51/42* | (2006.01) | |
| *C07C 59/84* | (2006.01) | |
| *C07D 211/22* | (2006.01) | |
| *C07C 51/02* | (2006.01) | |
| *C07C 51/41* | (2006.01) | |
| *C07C 51/43* | (2006.01) | |
| *C07C 59/86* | (2006.01) | |
| *C07C 59/88* | (2006.01) | |

(52) U.S. Cl.
CPC .................. *C07C 51/42* (2013.01); *C07C 51/02* (2013.01); *C07C 51/41* (2013.01); *C07C 51/412* (2013.01); *C07C 51/43* (2013.01); *C07C 59/84* (2013.01); *C07C 59/86* (2013.01); *C07C 59/88* (2013.01); *C07D 211/22* (2013.01)

(58) Field of Classification Search
CPC .................................. C07C 51/42; C07C 59/84
See application file for complete search history.

(56) References Cited

U.S. PATENT DOCUMENTS

| | | | |
|---|---|---|---|
| 4,254,129 | A | 3/1981 | Carr et al. |
| 5,750,703 | A | 5/1998 | D'Ambra |
| 8,236,961 | B2 | 8/2012 | Scubla et al. |
| 2002/0007068 | A1* | 1/2002 | D'Ambra .................... 546/237 |
| 2005/0277775 | A1 | 12/2005 | Castaldi et al. |
| 2010/0228034 | A1 | 9/2010 | Attolino et al. |

FOREIGN PATENT DOCUMENTS

| | | | |
|---|---|---|---|
| IN | 1225DEL2006 | * | 5/2006 |
| WO | 03000658 | A1 | 1/2003 |
| WO | 2008012859 | A2 | 1/2008 |

OTHER PUBLICATIONS

Crystallization by Antisolvent Addition and Cooling by Giulietti et al. published on Sep. 19, 2012, online discussion Bluelight/Drug Discussion shulgin_jr published Jan. 3, 2010.*
Antisolvent Addition and Cooling by Giulietti et al. published on Sep. 19, 2012.*

* cited by examiner

*Primary Examiner* — Yong Chu
(74) *Attorney, Agent, or Firm* — Rothwell, Figg, Ernst & Manbeck, P.C.

(57) ABSTRACT

Process for the preparation of 2-phenyl-2-methyl propanoic acid derivatives, useful as intermediates in the preparation of fexofenadine hydrochloride.

14 Claims, No Drawings

PROCESS FOR THE PURIFICATION OF 2-PHENYL-2-METHYL-PROPANOIC ACID DERIVATIVES

The present invention relates to a process for the purification of 2-phenyl-2-methyl propanoic acid derivatives, in particular as substantially pure regioisomeric form, useful in the preparation of fexofenadine hydrochloride active pharmaceutical ingredient.

BACKGROUND ART

The use of 2-phenyl-2-methyl propanoic acid derivatives as intermediates in the preparation of fexofenadine and salts thereof is known, for example, from U.S. Pat. No. 4,254,129 and from U.S. Pat. No. 5,750,703. A key point in the preparation of fexofenadine according to known methods is the use of 2-[4-(4-chloro-butyryl)phenyl]-2-methylpropionic acid (CKA) and of 2-[(4-cyclopropyl-carbonyl)-phenyl]-2-methylpropionic acid (CPKA), in the form of substantially pure regioisomers.

According to U.S. Pat. No. 5,750,703, such intermediates are obtained through a process comprising:

a) reacting a compound of formula (I)

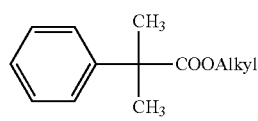
(I)

with a compound of formula (II)

Cl—(CH$_2$)$_3$—COX     (II)

wherein X is a halogen atom, in particular chlorine, to obtain a first mixture of isomers having formula (III)

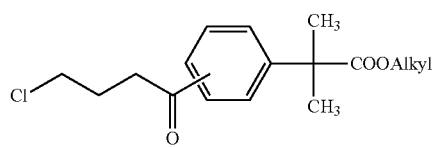
(III)

b) hydrolyzing a first mixture of isomers of formula (III) to obtain a second mixture of isomers of formula (IV)

(IV)

c) purifying said second mixture by fractional crystallization to obtain a substantially pure (para) isomer of formula (V), and finally

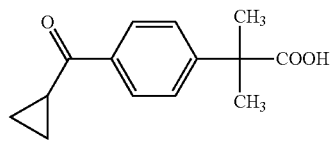
(V)

d) halogenating said substantially pure para-isomer of formula (V) to obtain, for example, 2-[4-(4-chloro-butyryl)phenyl]-2-methyl propionic acid of formula (VI)

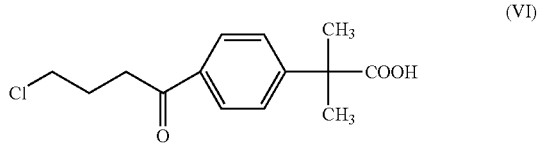
(VI)

According to the same patent, 2-[4-(4-chloro-butyryl)phenyl]-2-methyl propionic acid of formula (VI) (CKA) or 2-[(4-cyclopropyl-carbonyl)-phenyl]-2-methylpropionic acid of formula (V) (CPKA), or an alkyl ester thereof, is then reacted with a piperidine compound of formula (VII)

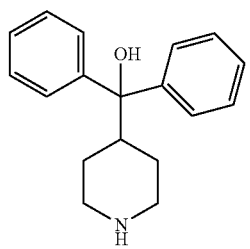
(VII)

to obtain a ketone compound of formula (VIII) or a alkyl ester thereof, (VIII)

from said compound of formula (VIII), if the case after hydrolysis of the ester group, by reduction of the carbonyl group, fexofenadine of formula (IX) is obtained

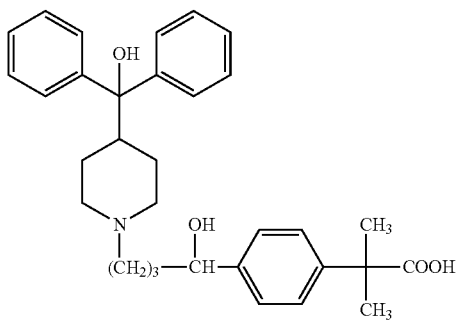

(IX)

Such process envisages some considerable drawbacks. For example, the substantially pure para regioisomer of formula (V) can be obtained by fractional crystallization from a great variety of salts thereof, for example from alkali salts, for example of sodium or potassium, or more preferably from an ammonium salt of formula $R_7R_8R_9N$, wherein $R_7$, $R_8$ and $R_9$ are H, or straight or branched optionally substituted $C_1$-$C_6$ alkyl, or a substituted phenyl. Said salt can also be a cinchonidine, quinine, quinidine, quinuclidine, brucine, thebaine or cinchonine salt. The cinchonidine salt is intended as preferred. The use of cinchonidine is illustrated in experimental example 2, which describes the purification of said second mixture by fractional crystallization to isolate a substantially pure para isomer of formula (V). Cause of the unfavorable ratio among the isomers, the purification results in a greater than 50% loss of material, experimental example 2 in fact shows a 33% yield. Moreover, since cinchonidine costs 10 times more than the commercial cost of substantially pure para isomer of formula (V), this procedure is expensive and deeply impacts on the cost of the final medicine.

The Indian patent application IN 1225DEL2006 partly solves the problem of obtaining 2-[4-(4-chloro-butyryl)phenyl]-2-methyl propionic acid of formula (VI), reported above, as substantially pure para-isomer, by a process comprising the purification of a mixture of meta and para isomers of a compound of formula (X)

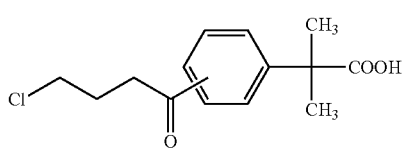

(X)

to remove the meta isomer, for example by slurry or by selective crystallization using an organic solvent, for example cyclohexane, hexane, heptane, isopropyl ether, preferably cyclohexane.

Even if the mentioned method is efficient, it is actually effective and usable only when the ratio between the meta and the para isomer is lower than 10/90, as reported in the experimental examples of the patent application.

The inventors of the present invention, when repeating the method disclosed in IN 1225DEL2006 and using regioisomeric mixtures of a compound of formula (X) with a higher content of meta isomer, that is mixtures wherein the ratio between the meta isomer and the para isomer is comprised between 15/85 and 50/50, obtained neither the formation of a precipitate of a compound of formula (VI), nor the purification of the mixture of meta and para regioisomers of the compound of formula (X).

Moreover, according to IN 1225DEL2006, said mixture wherein the ratio between the meta and the para isomer is lower than 10/90, is obtained through a long and tiresome method, comprising condensing a compound of formula (II), as defined above, with 1-acetoxy-2-methyl-2-phenylpropane of formula (XI)

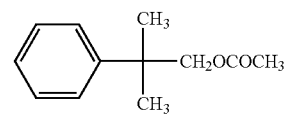

(XI)

to obtain a compound of formula (XII) containing more than 80% of para isomer,

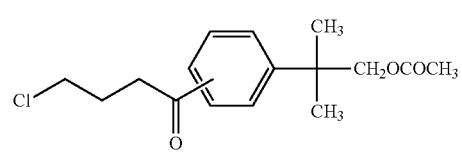

(XII)

acid hydrolysis of a compound of formula (XII) to obtain a compound of formula (XIII), and

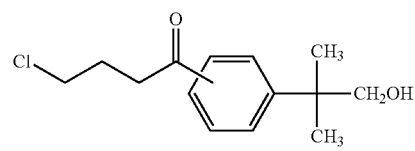

(XIII)

oxidation of said compound of formula (XIII) to obtain an acid of formula (X).

Even in this case, the cost of this process deeply impacts on the cost of the final medicine.

There is therefore the need of an alternative process, that can be validly industrially applicable for the preparation of 2-[4-(4-chloro-butyryl)phenyl]-2-methylproprionic acid (CKA) and of 4-(cyclopropyl-oxo-methyl)-α,α-dimethtlphenylacetic acid (CPKA), as substantially pure para regioisomers.

The inventors of the present invention have found that the preparation on industrial scale of said acids as substantially pure para regioisomers can be carried out by a purification process comprising their isolation by selective crystallization of an ammonium salt thereof.

SUMMARY OF THE INVENTION

The invention provides a purification process for obtaining a compound of formula (XIV), or a salt or ester thereof,

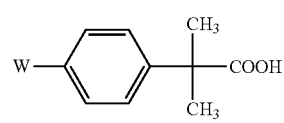

(XIV)

wherein W is a group chosen from

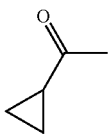

and Z—$(CH_2)_3$—CO—, wherein Z is a halogen atom, as substantially pure para-isomer, for example with a para/meta isomer ratio equal to or greater than 97/3, by a purification method comprising isolation by selective crystallization of an ammonium salt thereof. The method of the invention is useful in the preparation of fexofenadine or a pharmaceutically acceptable salt thereof.

DETAILED DESCRIPTION OF THE INVENTION

The invention provides, as a first object, a purification process for obtaining a compound of formula (XIV), as single para-isomer, or a salt or an ester thereof.

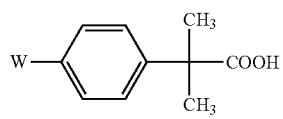 (XIV)

wherein W is a group chosen from

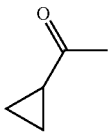

and Z—$(CH_2)_3$—CO—, wherein Z is a halogen atom, from a mixture of regioisomers of formula (XV)

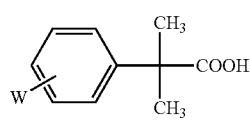 (XV)

wherein W is as defined above; said process comprising:
forming a salt of an ammonium compound of formula (XIV) with a compound of formula (XVI)

$R_1R_2R_3N$ (XVI)

wherein one or two of $R_1$, $R_2$ and $R_3$ is H, and the remaining one or each of the remaining ones of $R_1$, $R_2$ and $R_3$, being equal or different, is a $C_3$-$C_8$ alkyl group or $C_3$-$C_8$ cycloalkyl group;

separating by crystallization of the ammonium salt of the so obtained compound of formula (XIV);
recovering the solid; and, if the case,
converting the salt into the free acid, or into another salt or into an ester thereof.

A salt of a compound of formula (XIV) can be an ammonium salt as defined above, or a pharmaceutically acceptable salt thereof.

An ester of a compound of formula (XIV) is for example an alkyl ester, typically a $C_1$-$C_6$ alkyl ester, preferably a $C_1$-$C_4$ alkyl ester, in particular methyl ester, ethyl ester or isopropyl ester.

A $C_3$-$C_8$ alkyl group can be straight or branched alkyl group and is preferably a $C_3$-$C_5$ alkyl group, for example propyl, isopropyl, n-butyl, isobutyl, sec-butyl, tert-butyl, pentyl, isopentyl or neopentyl.

A $C_3$-$C_8$ cycloalkyl can be for example cyclopropyl, cyclopentyl or cyclohexyl.

A halogen atom Z is for example chlorine or iodine, preferably chlorine.

A compound of formula (XVI) is for example a base selected from propylamine, isopropylamine, di-isopropylamine, di-propylamine, butylamine, di-butylamine, di-secbutylamine, tert-butylamine, cyclopropylamine, 1-pentylamine, di-pentylamine (mixture of isomers), 2-pentylamine, cyclohexylamine, dicyclohexylamine.

The ratio between the meta and para isomer in a mixture of regioisomers of a compound of formula (XV) can be comprised for example between 5/95 and 50/50.

The stoichiometric ratio between a compound of formula (XVI), as defined above, and a compound of formula (XV) can be comprised between about 1.1 and about 0.4, preferably between about 0.7 and about 0.4, more preferably between about 0.6 and about 0.4.

The formation of an ammonium salt of a compound of formula (XIV) with a compound of formula (XVI) can be carried out in a solvent selected for example among a straight or branched $C_1$-$C_6$ alkanol; a $C_3$-$C_6$ ketone; a cyclic or acyclic ether; a $C_1$-$C_6$ alkyl ester of a carboxylic acid; acetonitrile; an aliphatic or aromatic hydrocarbon; a mixture of one of them with water or a mixture of two or three of them.

A $C_1$-$C_6$ alkanol is typically a straight or branched $C_1$-$C_4$ alkanol, for example methanol, ethanol, propanol, isopropanol, butanol, sec-butanol or is obutanol.

A $C_3$-$C_6$ ketone is for example acetone, methyl-ethylketone or methylisobutylketone.

An acyclic or cyclic ether is for example methyltertbutylether, tetrahydrofuran or dioxane.

A $C_1$-$C_6$ alkyl ester of a carboxylic acid, typically a $C_1$-$C_4$ alkyl-acetate is for example ethylacetate or isopropylacetate.

An aliphatic or aromatic hydrocarbon can be for cyclohexane, toluene, hexane or heptane.

Preferably the solvent medium is selected in the group comprising a $C_3$-$C_6$ ketone, in particular acetone; a $C_1$-$C_4$ alkanol, in particular methanol, isopropanol or a mixture thereof; toluene.

Said salification reaction can be carried out at a temperature comprised between about −5° C. and the reflux temperature of the solvent, preferably under stirring.

Surprisingly and in a completely unexpected way, the process of the present invention allows to directly obtain a compound of formula (XIV) as pure para regioisomer that is a useful intermediate in the preparation of fexofenadine. In fact, the inventors of the present application have found that when a mixture of regioisomers of formula (XV) is reacted with a compound of formula (XVI), only the ammonium salt of the para regioisomer compound of formula (XIV) forms, this way it can be easily separated by fractional crystallization. For this reason the process of the present invention can be efficiently and validly used in the preparation of fexofenadine.

The crystallization of an ammonium salt of a compound of formula (XIV) with a compound of formula (XVI) can be carried out by cooling the mixture or by adding an anti-solvent, preferably by cooling the mixture.

The crystallization of the ammonium salt, when carried out by cooling, can be performed bringing the temperature of the mixture from the dissolution temperature till a temperature comprised between about 0° C. and about 40° C., preferably between about 10° C. and 30° C., more preferably between about 20° C. and 25° C., typically at a cooling rate comprised between about 10° C./hour and about 1° C./hour.

An anti-solvent, that is a solvent wherein the crystalline solid is not soluble or is scarcely soluble, can for example be an aliphatic hydrocarbon for example a straight, branched or cyclic $C_5$-$C_7$ alkane, typically hexane, heptane or cyclohexane.

The recovery of the crystalline solid can be carried out according to known techniques, such as filtration or centrifugation.

The crystalline solid can be washed with a solvent as defined above, in particular the same solvent or mixture of solvents used in the formation of the ammonium salt.

The washing can be carried out directly on the filter or in centrifuge or suspending the solid at a temperature comprised between about 30° C. and the reflux temperature of the solvent, and leaving it under stirring for a time comprised between about one hour and six hours, at said temperature, then cooling the mixture at a temperature comprised between about 20° C. and about 25° C., and then repeating the filtration or centrifugation.

The solid can be dried according to known methods, for example in oven at a temperature comprised between about 30° C. and 55° C., under vacuum.

An ammonium salt of a compound of formula (XIV) can be converted into the free acid or into another salt, typically a pharmaceutically acceptable one, according to known methods. Similarly, an acid of formula (XIV) can be converted into a salt or into an alkyl ester according to known methods.

A compound of formula (XIV), and similarly a so obtained salt thereof with a compound of formula (XVI) in crystalline form, has a chemical purity equal to or greater than 97%, measured by HPLC, typically equal to or greater than 98%, comprising also the meta-isomer among the impurities.

A compound of formula (XIV), or a so obtained salt or ester thereof having a meta isomer content equal to or lower than 3%, preferably equal to or lower than 1.5%, can be defined as a substantially pure para-isomer.

If desired, such content can be further reduced by purifying once more the product according to the purifying process of the invention.

A further object of the invention is a salt of a compound of formula (XIV) with a compound of formula (XVI) in para-isomeric form, having a content of meta isomer equal to or lower than 3%, preferably equal to or lower than 1.5%, if the case in solid form, in particular in crystalline form.

Examples of an ammonium salt of the compound of formula (XIV), in substantially pure para-isomeric form are:

The salt of 2-[4-(4-chloro-butyryl)phenyl]-2-methylpropionic acid (CKA) with a base selected from propylamine, isopropylamine, di-isopropylamine, di-propylamine, butylamine, di-butylamine, di-secbutylamine, tert-butylamine, cyclopropylamine, 1-pentylamine, di-pentylamine (mixture of isomers), 2-pentylamine, cyclohexylamine and dicyclohexylamine; and The salt of 4-(cyclopropyl-oxo-methyl)-α,α-dimethylphenyl acetic acid (CPKA) with a base selected from propylamine, isopropylamine, di-isopropylamine, di-propylamine, butylamine, di-butylamine, di-secbutylamine, tert-butylamine, ciclopropylamine, 1-pentylamine, di-pentylamine (mixture of isomers), 2-pentylamine, cyclohexylamine and dicyclohexylamine.

The dimensions of the crystals of a compound of formula (XIV), and similarly of a salt of a compound of formula (XVI), as obtainable according to the process disclosed above is characterized by a $D_{50}$ value comprised between about 25 and 250 µm. If desired, such value can be reduced by micronization or fine grinding.

The experimental examples show both the high yield of the method of preparation and the high isomeric purity of the so obtained compound of formula (XIV). These results and the inexpensiveness of the bases of formula (XVI) and the easiness of purification method make the method very advantageous for preparing a compound of formula (XIV) on an industrial scale with a high chemical yield and both high chemical and isomeric purity.

A compound of formula (XIV), as single para-isomer, wherein W is a

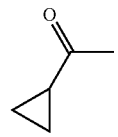

group can be converted to another compound of formula (XIV) wherein W is a Z—$(CH_2)_3$—CO—, group wherein Z is a halogen atom, in particular chlorine, according to known methods.

A compound of formula (XIV), as single para-isomer, wherein W is a

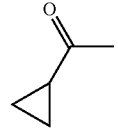

group is a compound of formula (V), as defined above.

A compound of formula (XIV) wherein W is a Z—$(CH_2)_3$—CO— group, and Z is a chlorine atom is a compound of formula (VI), as defined above.

According to a further embodiment, the invention provides a method for preparing fexofenadine or a salt thereof, which comprises the use of 2-[4-(4-chloro-butyryl)phenyl]-2-methyl propionic acid of formula (VI) or a $C_1$-$C_6$ alkyl ester thereof, with a high chemical and enantiomer purity, as herein obtained.

A further object of the invention is therefore a method for the preparation of fexofenadine, having formula (IX) or a pharmaceutically acceptable salt thereof, comprising:

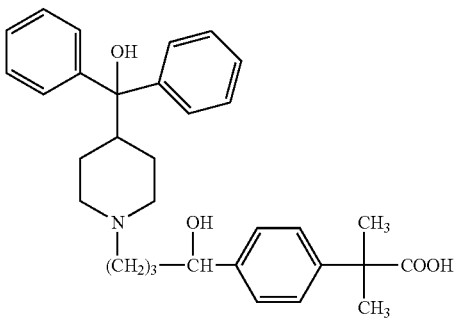

reacting an alkyl ester of a compound of formula (XIV), wherein W is a Z—(CH$_2$)$_3$—CO— group, and Z is a halogen atom, as single para-isomer, obtained according to the purification method of the present invention, with a piperidine compound of formula (VII)

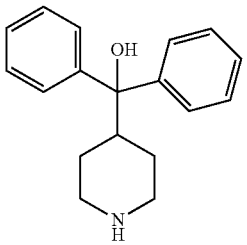

to obtain the respective alkyl ester of a ketone compound of formula (VIII)

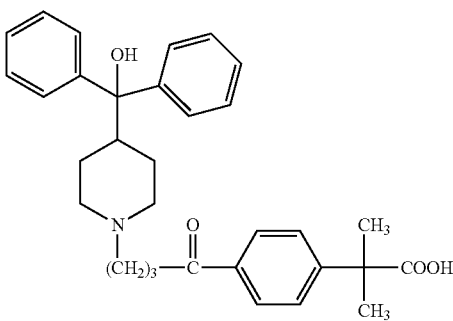

hydrolyzing the ester group and reducing the carbonyl group, and, if the case, converting a compound of formula (IX) thus obtained to a salt thereof.

An alkyl ester of the 2-[4-(4-chloro-butyryl)phenyl]-2-methyl propionic acid of formula (XIV) or a ketone compound of formula (VIII) is typically a C$_1$-C$_6$ alkyl ester, preferably a C$_1$-C$_4$ alkyl ester, in particular methyl, ethyl or isopropyl ester.

The reaction between an alkyl ester of 2-[4-(4-chloro-butyryl)phenyl]-2-methyl propionic acid of formula (XIV) with a compound of formula (VII) to obtain the alkyl ester of a ketone compound of formula (VIII), the hydrolysis of the ester group and the reduction of the carbonyl group in said compound to obtain fexofenadine, and if the case its conversion to a salt thereof, can be carried out according to known methods, for example as reported in U.S. Pat. No. 5,750,703.

A compound of formula (XV), can be prepared, for example according to U.S. Pat. No. 5,750,703 or to IN 1225DEL2006.

The following examples illustrate the invention.

EXAMPLE 1

Typical procedure for preparing the salt of CPKA (cyclopropyl keto acid) with cyclohexylamine (CHA) or with dicyclohexylamine (DCHA).

500 g of intermediate CPKA, composed of a mixture of about 1:1 of meta and para isomers, are dissolved in 4 volumes (2000 ml) of solvent. The mixture is brought to the given temperature (see Table 1 below), then the amine is dropped in about 30 minutes. The formation of the precipitate is observed. The mixture is left under stirring for 2 hours and then cooled to about 20° C. in about 20 hours. It is filtered off and carefully washed passing the solvent through the cake on the filter, or by slurry in the solvent. The obtained solid is dried in oven at about 60° C.

The following Table 1 illustrates examples of different working conditions and the obtained results.

TABLE 1

| Crystallization solvent | Temperature | Amine | Eq amine Vs. eq CPKA | Washing solvent | p:m Isomer | Yield (on isomer p) |
|---|---|---|---|---|---|---|
| Acetone | 25-45° C. | DCHA | 0.50 | Acetone | 93:7 | 69% |
| toluene | 100-110° C. | CHA | 0.50 | toluene | 97:3 | 61% |
| Isopropanol | 25-80° C. | CHA | 0.50 | IPA/methanol 1:1 | 98:2 | 80% |
| Isopropanol | 22-15° C. | DCHA | 1.01 | Isopropanol | 72:28 | 65% |
| IPA with 10% MeOH | 20-70° C. | CHA | 0.55 | Methanol | 98:2 | 67% |

IPA means isopropyl alcohol. MeOH means methanol.

CPKA salt with cyclohexylamine:

1H NMR (400 MHz, DMSOd6): d 7.91 (2H, d, J=8.7 Hz); 7.48 (2H, d, J=8.7 Hz); 2.83 (1H, m); 2.69 (1H, m); 2.78 (2H, m); 1.90-1.50 (5H, m); 1.40 (6H, s); 1.30-0.90 (9H, m).

Analogously the salts of CPKA with the following bases can be obtained:

propylamine, is opropylamine, di-propylamine, butylamine, di-butylamine, di-secbutylamine, tert-butylamine, cyclopropylamine, 1-pentylamine, di-pentylamine (mixture of isomers) and 2-pentylamine.

EXAMPLE 2

Typical procedure for the preparation of a salt of CKA (chloro keto acid) with Dicyclohexylamine (DCHA).

500 g of intermediate CKA, composed by a mixture of meta and para isomers of about 1:1, are dissolved in 4 volumes (2000 ml) of solvent. The mixture is brought to the given temperature, and then dicyclohexylamine is dropped in about 30 minutes. The formation of a precipitate is observed. The mixture is cooled, filtered and carefully washed passing the solvent through the cake on the filter, or by slurry in the solvent. The obtained solid is dried in oven at about 50° C.

The following Table 2 illustrates the working conditions and the obtained results.

TABLE 2

| Crystallization solvent | Volumes | T | Amine | Eq amine Vs. Eq. CKA | Washing solvent | p/m Isomer | Yield (on para isomer) |
|---|---|---|---|---|---|---|---|
| Acetone | 4 | 30-25° C. | DCHA | 0.98 | Acetone | 98.2:1.8 | 77% |

CKA salt of dicyclohexylamine:
1H NMR (400 MHz, CDCl3): d 7.90 (2H, d, J=8.1 Hz); 7.55 (2H, d, J=8.1 Hz); 3.67 (2H, t, J=6.6 Hz); 3.14 (2H, t, J=6.6 Hz); 2.78 (2H, m); 1.85-1.60 (10H, m); 1.55 (6H, s); 1.40-1.00 (10H, m).

Analogously the salts of CKA with the following bases can be obtained: propylamine, isopropylamine, di-propylamine, butylamine, di-butylamine, di-secbutylamine, tert-butylamine, cyclopropylamine, 1-pentylamine, di-pentylamine (mixture of isomers), 2-pentylamine and cyclohexylamine.

EXAMPLE 3

Typical procedure of preparation of the salt of CKA (chloro keto acid) with di-isopropylamine.

7.8 g of di-isopropylamine (1 equivalent) are added to 20 g of mixture of chloro-keto acid (CKA) in 80 ml of acetone. The mixture is concentrated till the CKA (chloro keto acid) salt with di-isopropylamine is obtained as a solid, which is isolated.

Analogously, a salt of CKA with each of the following bases can be obtained: propylamine, isopropylamine, di-propylamine, butylamine, di-butylamine, di-secbutylamine, tert-butylamine, cyclopropylamine, 1-pentylamine, di-pentylamine (mixture of isomers) and 2-pentylamine.

The invention claimed is:

1. A purification process for obtaining a compound of formula (XIV) as a single para-isomer, a salt thereof, or an ester thereof,

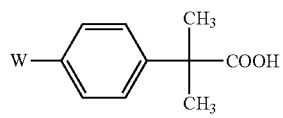
(XIV)

wherein W is a group chosen from

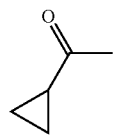

and Z-(CH$_2$)$_3$-CO-, in which Z is a halogen atom, from a mixture of regioisomers of a compound of formula (XV)

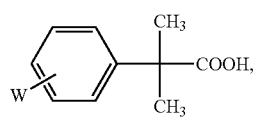
(XV)

said process comprising:
selectively preparing an ammonium salt of a compound of formula (XIV), by reacting the mixture of regioisomers of formula (XV) with an amine selected from the group consisting of cyclopropylamine, cyclohexylamine, and dicyclohexylamine;
wherein the ratio of the meta-isomer to the para-isomer in the mixture of regioisomers of a compound of formula (XV) ranges from about 5/95 to about 50/50;
separating by crystallization the ammonium salt of the compound of formula (XIV);
recovering the ammonium salt; and optionally converting the ammonium salt into the free acid or into another salt thereof, or into an ester thereof.

2. The process according to claim 1, wherein the stoichiometric ratio of the amine to the compound of formula (XV) ranges from about 1.1 to about 0.4.

3. The process according to claim 1, wherein the stoichiometric ratio of the amine to the compound of formula (XV) ranges from about 0.7 to about 0.4.

4. The process according to claim 1, wherein the ammonium salt of the compound of formula (XIV) is obtained in a solvent medium selected from a straight or branched $C_1$-$C_6$ alkanol, or a mixture thereof; a $C_3$-$C_6$ ketone; an acyclic or cyclic ether; a $C_1$-$C_6$ alkyl-ester of a carboxylic acid; acetonitrile; an aliphatic or aromatic hydrocarbon, or a mixture of one of the above solvents with water or a mixture of two or three thereof.

5. The process according to claim 4, wherein the straight or branched $C_1$-$C_6$ alkanol is a $C_1$-$C_4$ alkanol; and the $C_3$-$C_6$ ketone is acetone.

6. The process according to claim 1, wherein the separation of the ammonium salt of the compound of formula (XIV) by crystallization is carried out by cooling the reaction mixture, bringing the temperature of the mixture from the dissolution temperature up to a temperature ranging from about 0° C. to about 40° C.

7. The process according to claim 1, wherein the separation of the ammonium salt by crystallization is carried out by cooling the reaction mixture, bringing the temperature of the mixture from the dissolution temperature up to a temperature ranging from about 10° C. to about 30° C.

8. The process according to claim 1, wherein the separation of the ammonium salt of the compound of formula (XIV) by crystallization is carried out by adding an aliphatic hydrocarbon as an antisolvent.

9. The process according to claim 1, wherein the aliphatic hydrocarbon is selected from a straight, branched or cyclic $C_5$-$C_7$ alkane.

10. The process according to claim 1, wherein the compound of formula (XIV), a salt thereof or an ester thereof, thus obtained, has a meta-isomer content equal to or lower than 3%.

11. The process according to claim 10, wherein the meta-isomer content equal to or lower than 1.5%.

12. The process according to claim 1, further comprising:
reacting the single para-isomer of an alkyl ester of a compound of formula (XIV),

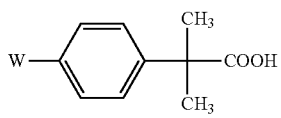

(XIV)

in which W is Z-(CH$_2$)$_3$-CO-, and Z is a halogen atom, with a compound of formula (VII)

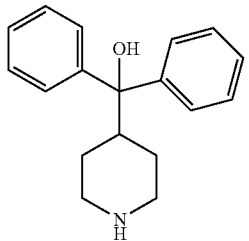

(VII)

to obtain an alkyl ester of a compound of formula (VIII)

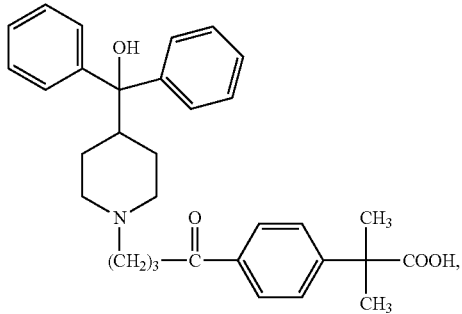

(VIII)

hydrolyzing the ester group and reducing the carbonyl group in said compound of formula (VIII) to afford a compound of formula (IX)

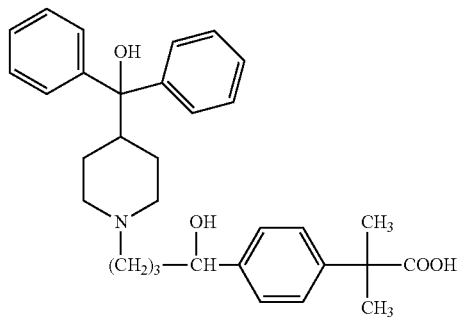

(IX)

and, optionally, converting the compound of formula (IX) into a salt thereof.

13. The process of claim 1, wherein the ratio of the meta-isomer to the para-isomer in the mixture of regioisomers of the compound of formula (XV) ranges from about 15/85 to about 50/50.

14. The process of claim 1, wherein the compound of formula (XIV) as a single para-isomer, a salt thereof, or an ester thereof is obtained in at least 60% yield.

* * * * *